United States Patent
Bastia

(10) Patent No.: US 9,629,637 B2
(45) Date of Patent: Apr. 25, 2017

(54) DEVICE FOR IMPLANTING A PROSTHESIS IN A TISSUE

(71) Applicant: THD S.P.A., Correggio (IT)

(72) Inventor: Filippo Bastia, Sozzigalli di Soliera (IT)

(73) Assignee: THD S.P.A., Correggio (IT)

( * ) Notice: Subject to any disclaimer, the term of this patent is extended or adjusted under 35 U.S.C. 154(b) by 174 days.

(21) Appl. No.: 14/725,959

(22) Filed: May 29, 2015

(65) Prior Publication Data

US 2015/0257762 A1     Sep. 17, 2015

Related U.S. Application Data

(62) Division of application No. 13/403,460, filed on Feb. 23, 2012.

(30) Foreign Application Priority Data

Feb. 25, 2011  (IT) .............................. MO2011A0041
Feb. 25, 2011  (IT) .............................. MO2011A0042
Feb. 25, 2011  (IT) .............................. MO2011A0043

(51) Int. Cl.
| | |
|---|---|
| *A61B 17/10* | (2006.01) |
| *A61B 17/12* | (2006.01) |
| *A61B 17/34* | (2006.01) |
| *A61B 17/00* | (2006.01) |
| *A61F 2/00* | (2006.01) |

(52) U.S. Cl.
CPC .... *A61B 17/1219* (2013.01); *A61B 17/00234* (2013.01); *A61B 17/12036* (2013.01); *A61B 17/3468* (2013.01); *A61B 2017/0046* (2013.01); *A61B 2017/00398* (2013.01); *A61B 2017/00805* (2013.01); *A61B 2017/00818* (2013.01); *A61B 2017/00827* (2013.01); *A61B 2017/00898* (2013.01); *A61B 2017/1205* (2013.01); *A61B 2017/12054* (2013.01); *A61F 2/0036* (2013.01)

(58) Field of Classification Search
CPC ... A61B 17/068; A61B 17/10; A61B 17/0401; A61B 17/064; A61B 17/00234
See application file for complete search history.

(56) References Cited

U.S. PATENT DOCUMENTS

| | | |
|---|---|---|
| 4,774,091 A | 9/1988 | Yamahira et al. |
| 4,799,921 A | 1/1989 | Johnson et al. |
| (Continued) | | |

FOREIGN PATENT DOCUMENTS

| | | |
|---|---|---|
| EP | 0 153 569 A2 | 9/1985 |
| EP | 1222903 A1 | 7/2002 |
| (Continued) | | |

*Primary Examiner* — Thomas J Sweet
*Assistant Examiner* — Tiffany Shipmon
(74) *Attorney, Agent, or Firm* — Pearne & Gordon LLP

(57) ABSTRACT

A device for implanting a prosthesis 12 in a body tissue equipped with a tubular element 7, within which a prosthesis 12 can slide, and a pressure element 16 for moving said prosthesis 12. The device also comprises a cartridge 5 provided with a seat 31 at its interior, such seat housing the prosthesis 12 and movable under the action of a pusher element 13 from a first position, in which the seat 31 is not facing the tubular element 7, to a second position, in which the seat 31 is in communication with the tubular element 7 in order to allow the insertion of the prosthesis 12 inside the tubular element 7 upon command of the pressure element 16.

16 Claims, 5 Drawing Sheets

(56) References Cited

U.S. PATENT DOCUMENTS

| | | |
|---|---|---|
| 4,802,479 A | 2/1989 | Haber et al. |
| 5,021,241 A | 6/1991 | Yamahira et al. |
| 5,106,370 A | 4/1992 | Stewart |
| 5,147,295 A | 9/1992 | Stewart |
| 5,611,811 A | 3/1997 | Goldberg |
| 5,817,075 A | 10/1998 | Giungo |
| 6,102,844 A | 8/2000 | Ravins et al. |
| 6,245,052 B1 | 6/2001 | Orth et al. |
| 6,428,463 B1 | 8/2002 | Ravins et al. |
| 6,432,035 B1 | 8/2002 | Ravins et al. |
| 6,440,141 B1 | 8/2002 | Phillippon |
| 6,508,755 B1 | 1/2003 | Ravins et al. |
| 6,592,508 B1 | 7/2003 | Ravins et al. |
| 2002/0002360 A1 | 1/2002 | Orth et al. |
| 2002/0026195 A1 | 2/2002 | Layne et al. |
| 2002/0052653 A1 | 5/2002 | Durgin |
| 2002/0123808 A1 | 9/2002 | Li |
| 2002/0188353 A1 | 12/2002 | Phillipon |
| 2002/0193656 A1 | 12/2002 | Ravins et al. |
| 2003/0097144 A1 | 5/2003 | Lee |
| 2003/0192558 A1 | 10/2003 | Durgin |
| 2003/0192559 A1 | 10/2003 | Durgin |
| 2003/0196670 A1 | 10/2003 | Durgin |
| 2005/0090852 A1 | 4/2005 | Layne et al. |
| 2006/0100640 A1 | 5/2006 | Bolduc |
| 2006/0247578 A1 | 11/2006 | Arguedas et al. |
| 2007/0123797 A1 | 5/2007 | Kranse |
| 2008/0140086 A1 | 6/2008 | Moore et al. |
| 2008/0208165 A1 | 8/2008 | Orth et al. |
| 2009/0018505 A1 | 1/2009 | Arguedas et al. |
| 2009/0099638 A1 | 4/2009 | Grewe |
| 2010/0256596 A1 | 10/2010 | Chomas |
| 2011/0144622 A1 | 6/2011 | Orth et al. |
| 2012/0310320 A1 | 12/2012 | Gill et al. |

FOREIGN PATENT DOCUMENTS

| | | |
|---|---|---|
| GB | 2199247 A | 7/1988 |
| JP | H05-000144 A | 1/1993 |
| JP | 2010-516302 A | 5/2010 |
| WO | 9858698 A1 | 12/1998 |
| WO | 9933512 A2 | 7/1999 |
| WO | 0002616 A1 | 1/2000 |
| WO | 0165996 A2 | 9/2001 |
| WO | 0176492 A1 | 10/2001 |
| WO | 2008/085763 A1 | 7/2008 |

Fig. 9a
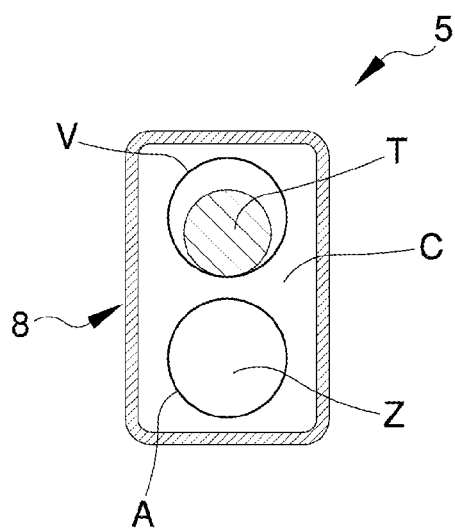
Fig. 9b
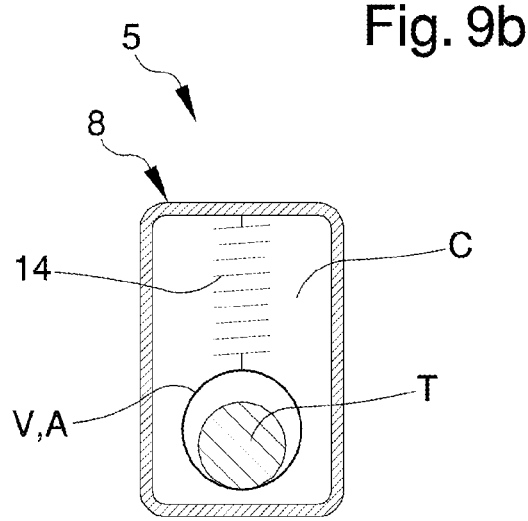
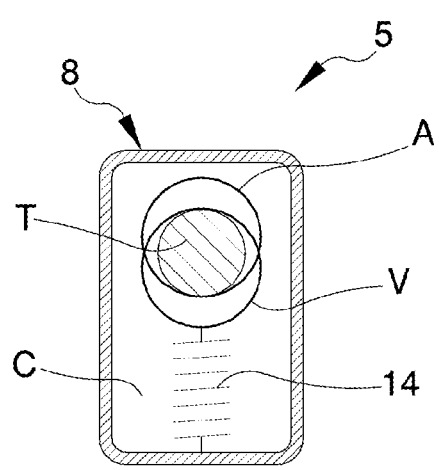
Fig. 9c

DEVICE FOR IMPLANTING A PROSTHESIS IN A TISSUE

The invention concerns a device for implanting a prosthesis inside a tissue delimiting a channel of the human body, in order to cause a narrowing of such channel, i.e. a reduction of the relative cross section. The invention also concerns a functioning method for the device.

The device according to the invention can be used for example for implanting the prosthesis close to the anal canal, if it is desired to decrease the size of the relative cross section in order to treat a patient affected with fecal incontinence.

Alternatively, the device according to the invention can be used for implanting the prosthesis in tissues delimiting the urinary canal. The narrowing deriving therefrom is useful for treating a patient affected with urinary incontinence.

In addition, the device according to the invention can be used for implanting the prosthesis in the mucous of the esophagus if it is desired to treat a patient affected by gastro-esophagus reflux.

The prosthesis implanted by using the device according to the invention can be obtained in a known polymer material such as hyexpan, i.e. a material having the capacity to absorb high quantities of liquid and consequently be swollen. When a prosthesis of this type is implanted in a tissue that delimits a channel of the patient's body, the material constituting it absorbs the body liquids, causing a swelling of the prosthesis itself. In such a manner, the narrowing of the channel is produced, whose free cross section decreases. The passage of substances, liquids or solids through the channel is consequently blocked.

US 2002/0052653 describes a device for implanting a prosthesis close to the gastroesophageal junction of a patient. The device comprises a hollow member, at whose interior a passage is provided in which one or more prostheses can be received to be implanted in the body of the patient. The device also comprises a pusher element, arranged inside the hollow member and movable with respect to the latter, so as to make the prosthesis exit through a distal end of the hollow member, in order to position the prosthesis at the desired point of the patient's body.

In order for the prosthesis to exit outward from the distal end of the hollow member, it is possible to push the pusher element towards the distal end. Alternatively to that stated above, it is also possible to retreat the hollow member towards the operator while the pusher element remains in contact with the prosthesis.

A first defect of the device described in US 2002/0052653 is that such device does not ensure a precise positioning of the prosthesis in the body of the patient, particularly when the hollow member is retreated with respect to the pusher element. Indeed, the hollow member might not be retreated enough, in which case the hollow member is stopped while a portion of the prosthesis is still situated therein. If this occurs, when the operator moves the device away from the body of the patient, the prosthesis tends to be driven by the hollow member and its position is consequently altered in an undesired manner.

It is also possible that the opposite situation occurs, i.e. that the hollow member is overly retreated with respect to the pusher element. This situation is problematic, especially if multiple prostheses are present inside the hollow member, such prostheses arranged behind each other in order to be inserted in the body of the patient in subsequent instances. Indeed, if the hollow member moves back too much, not only does the desired prosthesis exit therefrom but also a portion of the successive prosthesis. The latter, in contact with the body liquids, is swollen and can no longer be fully reinserted inside the hollow member.

A second defect of the device described in US 2002/0052653 is that such device does not isolate the prosthesis during the steps in preparation for the insertion of the same in the patient's body.

During the insertion and positioning of the hollow member inside the human tissue, blood, organic liquids and tissue fragments might enter inside the hollow member until they come into contact with the prosthesis.

The contact of the blood and the organic liquids with the prosthesis can generate the swelling of the same, before this has exited outward from the hollow body, with consequent difficulty in sliding inside the hollow body.

In some case, the swelling of the prosthesis can generate the occlusion of the hollow body and phenomena of pointing of the prostheses inside the hollow body.

In order to avoid the abovementioned problems, it is possible to preliminarily carry out the insertion of the hollow body and the positioning of the same in the human tissue, and subsequently proceed with the insertion of the prosthesis in the hollow body.

Such method is not free of risks of infection of the prosthesis from a bacteriological standpoint.

In addition, the aforesaid successive loading of the prosthesis renders the surgical operation difficult and imprecise, lengthening the operating times and complicating the operating steps of the operation.

Another defect of the device described in US2002/0052653 is the conformation of the terminal portion adapted to penetrate the body tissue in order to generate, inside the same, the prosthesis insertion channel.

The hollow conformation of the terminal portion does not allow the isolation of the tubular body interior from blood, organic liquid and tissue fragments.

In addition, the hollow internal conformation and the asymmetric external conformation does not facilitate the insertion of the hollow element inside the body tissue.

One object of the invention is to improve the devices for implanting prostheses, particularly prostheses of the type capable of absorbing a liquid and consequently swelling, in a human tissue, particularly a tissue delimiting a body channel, so as to cause a narrowing of the channel.

A first object is to provide a device which allows precisely positioning the prostheses in the tissue.

Further object is to reduce the risk that, when one implants a prosthesis in a tissue, the prosthesis is not completely released inside the tissue, or reduce the risk that a portion of a possible successive prosthesis is also released.

A second object is to provide a device that allows isolating the prostheses before their placement inside human tissue.

Another object is to provide for a device, bearing at least one prosthesis, adapted to limit as much as possible the contact between the prosthesis and organic liquids released by the body tissue.

A third object is to provide a device which allows an easy insertion of the tubular body in the body tissue, protecting the integrity of the prosthesis.

The invention can be better understood and actuated with reference to the enclosed drawings, which illustrate an exemplifying and non-limiting embodiment thereof, in which:

FIG. 9a is a cross section taken along the plane I-I of FIG. 3 illustrating a particular structural detail of the cartridge in a first position.

FIG. 9b is a cross section taken along the plane II-II of FIG. 5 illustrating a structural detail of the cartridge in a second position.

FIG. 9c is a cross section of a second variant of the cartridge in an intermediate time instant with respect to that of FIG. 9a and that of FIG. 9b.

FIG. 1 shows a device 1 for implanting a prosthesis in a body tissue, particularly in a tissue that delimits a channel of the body of a patient, e.g. the anal canal, or the urinary canal, or the esophagus canal.

Figure 8:
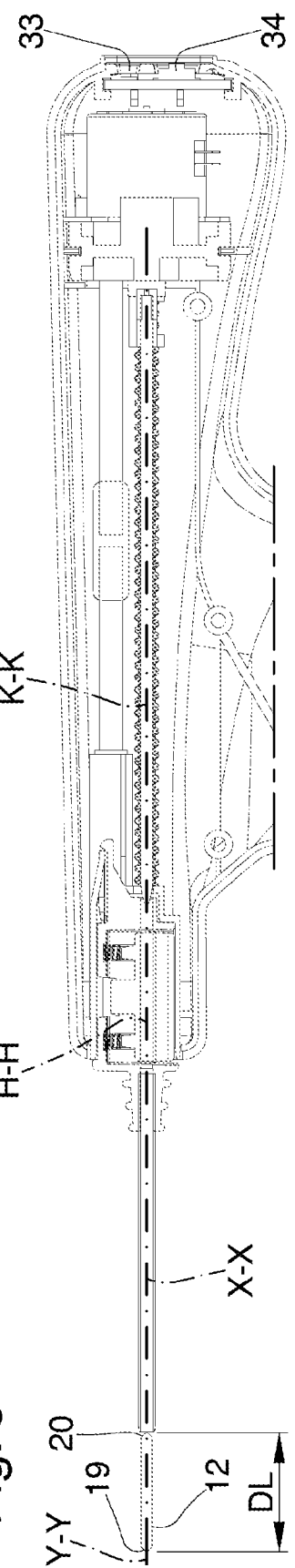
FIG. 8 is a section like that of FIG. 3, showing an upper portion of the device of FIG. 1 at the end of the aforesaid release position.

The prosthesis is shown in particular in FIG. 8, where it is indicated with the reference number 12. The prosthesis 12 can have elongated shape, e.g. cylindrical or prismatic, and it can be obtained with so-called hyexpan material.

Said prosthesis 12 preferably has elongated form with extension direction along an axis Y-Y.

Said prosthesis 12 has cross section with area T and preferably has cylindrical shape.

The prosthesis 12 has a front end 19, which first exits outward from the device 1, and a rear end 20, which exits outward from the device 1 last. The front end 19 and the rear end 20 are placed at a mutual distance DL, which defines a longitudinal size of the prosthesis 12.

Figure 1:
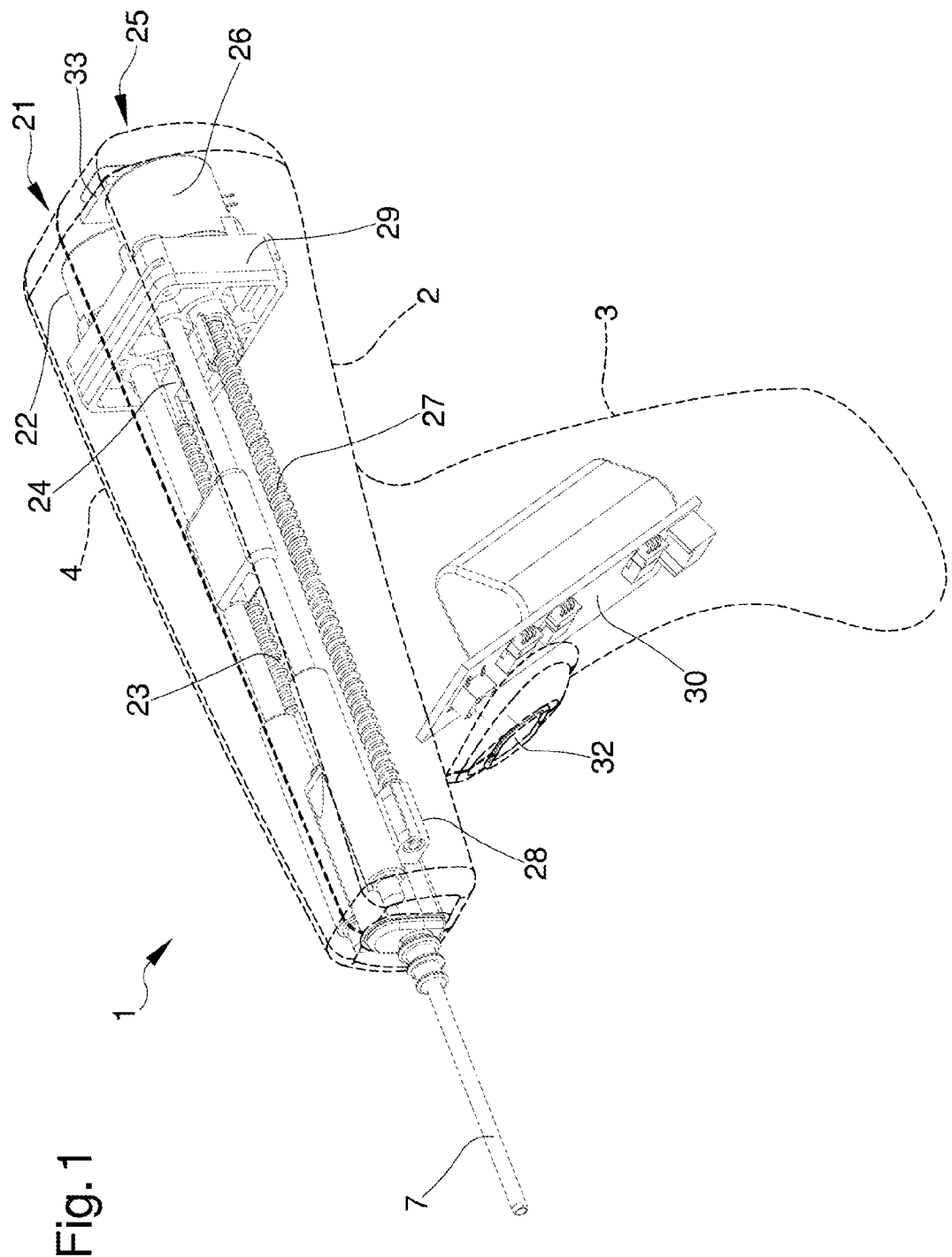
FIG. 1 is a perspective view showing a device for implanting a prosthesis in a tissue delimiting a body channel of a patient.

The device 1 comprises an applicator pistol 2, whose border was indicated with a dashed line in FIG. 1 for the sake of clarity. The applicator pistol 2 is provided with a grasping portion 3, adapted to be grasped by an operator, and an operative portion 4, in which the mechanisms are housed that allow moving the prosthesis 12. The grasping portion 3 is projected from one side of the operative portion 4, transverse with respect to a main direction along which the operative portion 4 is extended.

Figure 2:
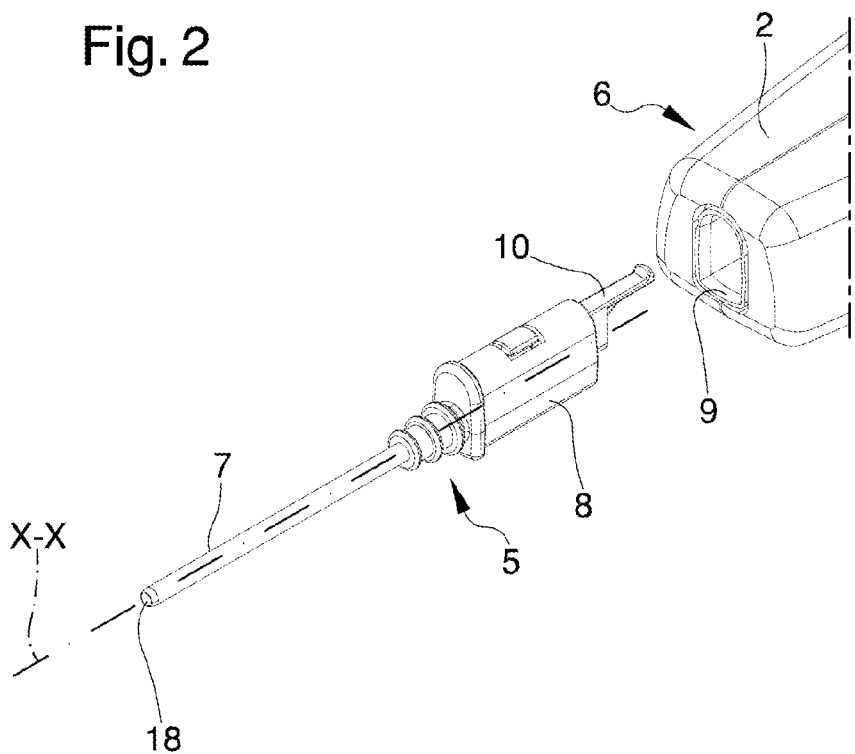
FIG. 2 is an interrupted perspective view, showing a front portion of an applicator pistol included in the device of FIG. 1 and a cartridge insertable in the applicator pistol.

The device 1 comprises a cartridge 5, more visible in FIG. 2, adapted to be mounted in a front terminal region 6 of the applicator pistol 2. The cartridge 5 comprises a tubular element 7 which, during use, is projected from the front terminal region 6.

Said tubular element 7 defines a channel Z at its interior; such channel has extension direction along a first axis X-X and cross section with area A, within which the prosthesis 12 can slide.

The tubular element 7 is provided with an open end 18, through which the prosthesis 12 can exit outward. The open end 18 is the end of the tubular element 7 arranged in a position far from the applicator pistol 2.

The cartridge 5 also comprises a support body 8 adapted to be introduced inside a hole 9 obtained in the frontal terminal region 6. The tubular element 7 is projected from a first end of the support body 8.

Said support body 8 defines a chamber C at its interior; such chamber is in liquid communication with the channel Z and comprises a seat 31, housing a prosthesis 12, movable inside the chamber C and described in more detail below.

The support body 8 can be equipped with fixing means 10 adapted to allow the cartridge 5 to be fixed to the applicator pistol 2. The fixing means 10 can comprise a tongue that is projected from a second end of the support body 8, the tongue being adapted to be engaged, e.g. snap-engaged, with a laminar element 11 of the applicator pistol 2, as shown in FIG. 3.

The tubular element 7 is slidable inside the support body 8 in a direction substantially parallel to an extension axis X-X of the tubular element 7, as will be explained in detail below.

Figure 3:
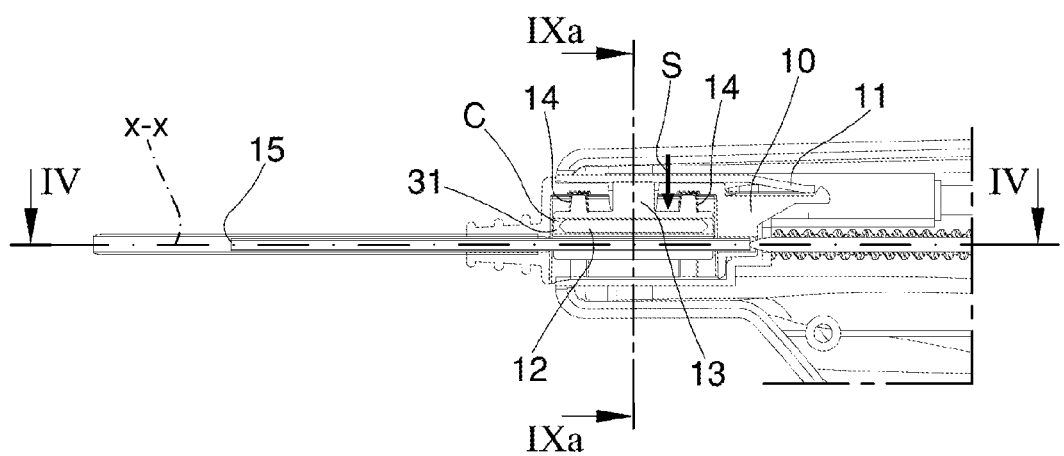
FIG. 3 is a section, taken along a vertical longitudinal plane, showing a front portion of a second embodiment of the device of FIG. 1 in a first trigger position.

As shown in FIG. 3, the device 1 comprises a pressure element 16, adapted to act on the rear end 20 of the prosthesis 12 in order to push the prosthesis 12 towards the body tissue where it must be inserted. Said pressure element 16, defined by a cylindrical body, has extension direction along an axis K-K parallel and coinciding to the extension axis X-X of the tubular element.

The pressure element 16 is slidable inside the tubular element 7.

In other words, the pressure element 16 is movable inside the channel Z in order to move the prosthesis 12.

In a first embodiment, the device 1 can be directly provided with the assembled cartridge 5.

Figure 4:
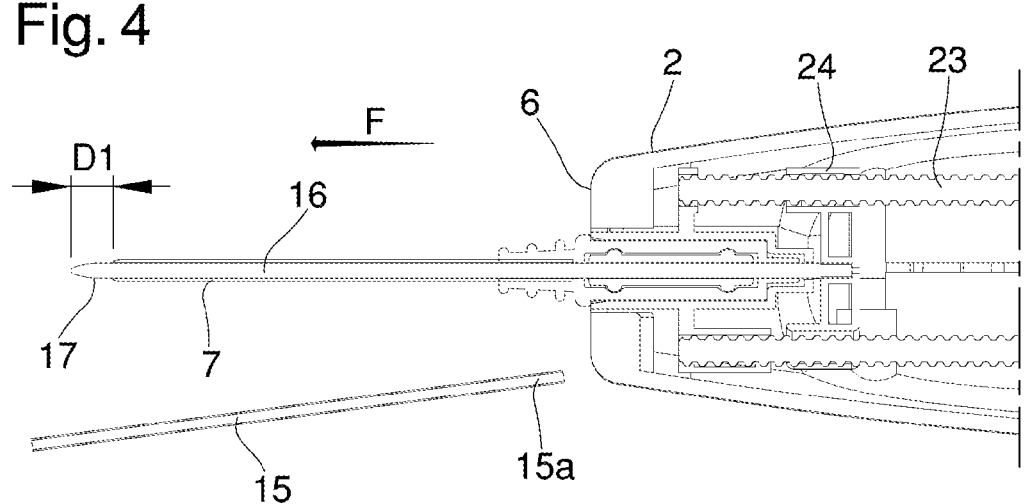
FIG. 4 is a section, taken along the plane IV-IV of FIG. 3, showing the front portion of a second embodiment of the device of FIG. 1 in a rest position, if the device is obtained according to a first embodiment, or in an advance position if the device is obtained according to the second embodiment.

In such case, the pressure element 16 is inserted inside the tubular body 7 (FIG. 4).

In a second embodiment, the device 1 can be provided with the cartridge 5 disassembled.

In such case, the pressure element 16 can be initially housed in the applicator pistol 2 in a manner such that, when the cartridge 5 is mounted on applicator pistol 2, the pressure element 16 is aligned with the tubular element 7 (FIG. 3).

As shown in FIG. 4, the pressure element 16 can be shaped like a needle and can be provided with a pointed end 17, adapted for piercing body tissue.

Said pointed end 17 is preferably closed in order to prevent blood and body tissue from entering inside the tubular body 7 and coming into contact with the prosthesis 12.

Said pointed end 17 has axial-symmetric extension with respect to the extension axis K-K of the pressure element 16.

In other words, the pointed portion 17 preferably has frustoconical shape with symmetry axis coinciding with the extension axis K-K of the pressure element 16.

In addition, the open end 18 of the tubular element 7 has tapered conformation towards the vertex of the pointed portion 17 of the pressure element 16.

The configurations of the pointed end 17 and the open end 18 prevent fragments of body tissue from entering inside the tubular body 7 during the insertion of the same inside the tissue.

In such a manner, during the sliding of the prosthesis 12 inside the tubular element 7, the fragments do not occupy the space between the external surface of the prosthesis 12 and the internal surface of the tubular element 7.

Consequently, the sliding of the prosthesis 12 inside the tubular element occurs without pointing and through the use of low-power motorized means.

The support body 8 can also comprise, in the second embodiment, a locking element 15, visible in FIGS. 3 and 4, for example having the form of a cylinder, possibly internally hollow. The locking element 15 is housed in a slidable manner inside the tubular element 7, so as to be aligned with the pressure element 16. In particular, the locking element 15 can be pushed towards the open end 18 by the pressure element 16, so as to be removed from the device 1.

More precisely, the locking element 15 has at least one hollow terminal section 15a, facing the pressure element 16, in order to allow the pointed end 17, during the movement of the pressure element 16, to engage the locking element 15 in order to push it outside the tubular element 7.

In other words, when the pressure element 16 impacts the locking element 15, its pointed end 17 is inserted inside the hollow terminal section 15a, facilitating the engagement of the pressure element 16 with the locking element 15.

The function of the locking element 15 will be better explained below.

As shown in FIG. 3, inside the support body 8, the seat 31 is obtained in which a prosthesis 12 can be housed that is ready to be implanted in the body of the patient.

Said seat 31 has extension direction along an axis H-H, coinciding with the extension axis Y-Y of the prosthesis 12, and cross section with area V.

A pusher element 13 is active on the seat 31, inside the cartridge 5.

Said pusher element 13 facilitates the movement the seat 31, inside the chamber C, from a first position to a second position.

More precisely, said pusher element 13 is defined by elastic means 14 adapted to generate a push of the seat 31 from the first position to the second position.

Said elastic means 14 facilitate a push of the seat 31 according to a push direction S incident on the first axis X-X of the channel Z.

In the first position, the seat 31 is not facing the channel Z.

As illustrated in FIG. 9a, in said first position the area V of the cross section of the seat 31 is outside the area A of the cross section of the tubular element 7.

In other words, the area V of the seat 31 does not intersect the area A of the tubular element.

In such time instant, the area of the cross section T of the seat 12 is outside the area A of the cross section of the tubular element 7.

In the case of prosthesis 12 with elongated form, housed in the suitably counter-shaped seat 31, the axis X-X of the channel Z in said first position is misaligned with respect to the axis H-H of the seat 31.

Still more in detail the axis H-H of the seat 31, and hence the axis Y-Y of the prosthesis 12, is parallel to the first axis X-X of the channel Z but does not coincide with the same.

The arrangement of the axis H-H of the seat 31, and hence of the prosthesis 12, with respect to the channel Z allows preventing the liquid communication between the channel Z and the seat 31.

This prevents the organic liquid, during the operations of insertion of the tubular element 7 inside the tissue, from flowing inside the channel Z and reaching the seat 31—hence coming into contact with the prosthesis 12.

In the second position, the seat 31 comes into communication with the channel Z.

Come illustrated in FIG. 9c, the area V of the cross section of the seat 31 at least partly intersects the area A of the cross section of the tubular element 7. In such time instant, the communication between the channel Z and the seat 31 is facilitated, adapted to ease the insertion of the prosthesis 12 inside the channel Z upon command of the pressure element 16.

If the area V of the cross section of the seat 31 is greater than the area A of the cross section of the tubular element 7, the second position, assumed by the seat 31, is illustrated in FIG. 9c.

If the area V of the cross section of the seat 31 is lower, or substantially equal to the area of the cross section of the tubular element 7, the second position assumed of the seat 31 is illustrated in FIG. 9b.

In both hypotheses, said second position is completely reached when the area T of the cross section of the prosthesis 12 is fully contained in the area A of the tubular element 7.

In the case of elongated prosthesis 12, contained inside the suitably counter-shaped seat 31, in said second position the first axis X-X of the channel Z is aligned with respect to the axis H-H of the seat 31.

Still more in detail, the axis H-H of the seat, and hence also the axis Y-Y of the prosthesis 12, is parallel to the axis X-X of the channel Z and coincides with the same.

The arrangement of the axis of the prosthesis 12, hence of the seat 31, with respect to the channel Z allows obtaining the liquid communication between the channel and the seat.

This allows, due to the subsequent action of the pressure element 16, described in more detail below, facilitating the insertion of the prosthesis 12 inside the channel Z and the subsequent exit from the channel Z.

Below, the two embodiments of the device 1 are described, having several components in common; for this reason, they are only described once during the embodiment discussion.

In a first embodiment, the seat 31 is positioned above the pressure element 16 which can be at least partly arranged in the chamber C.

More specifically, in such context of the first embodiment, the pressure element 16 is arranged, before the applicator pistol starts to function, in a rest position (illustrated in FIG. 4).

In said rest position, the pressure element 16 can be at least partly inside the chamber C.

In said rest position, the pusher element 13 pushes the seat 31 against the pressure element 16 by maintaining the latter in the first position.

In said rest position, the pressure element 16 is an obstacle to the facilitated push, along the direction S, from the pusher element 13 onto the seat 31.

As illustrated in FIG. 4, the pressure element 16 exits outward, with the pointed end 17 thereof, from the tubular element 7 by an amount D1.

In such case, the pressure element 16 is completely inserted inside the chamber C, crossing the same in order to reach the channel Z of the tubular element 7, entirely crossing it.

The device 1 also comprises first movement means 21 in order to move the pressure element 16 inside the tubular element 7 parallel to the axis X-X.

The first movement means 21, common to both embodiments, can comprise a first motor 22, e.g. of electric type, adapted to rotate a first worm screw 23. The first worm screw 23 is in turn engaged with a carriage 24 on which the pressure element 16 is mounted.

Said pressure element 16, in the first embodiment, is movable under the action of first movement means 21 from the rest position to a retreated position and from the retreated position to a loading position.

In said retreated position, the pressure element 16 is disconnected from the chamber C in order to allow the pusher means to move, along the direction S, the seat 31 in the second position.

Figure 6:
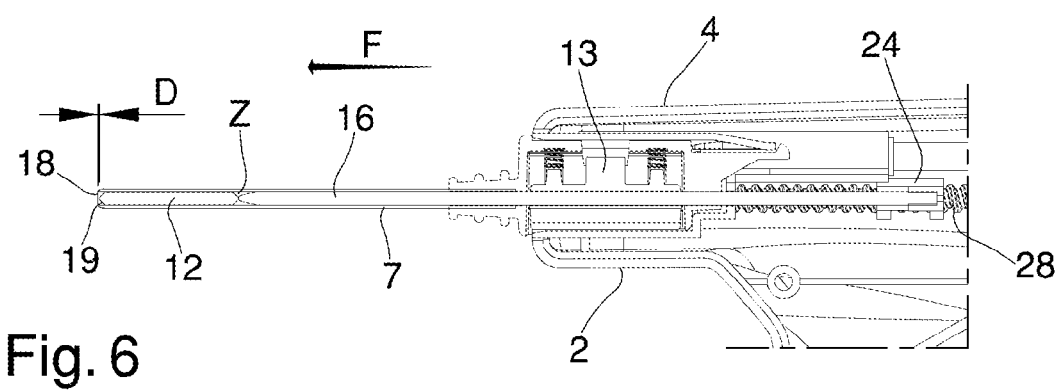
FIG. 6 is a section like that of FIG. 3, showing the front portion of the device of FIG. 1 in a loading position.

The first movement means 21 facilitate the movement of the pressure element 16, from the rest position to the retreated position (the latter visible in FIG. 6).

In other words, the first movement means 21 are programmed for moving pressure element 16 back outside the tubular body 7 and the chamber C in order to generate the liquid communication between the seat 31 and the channel Z and to allow the pusher element 13 to push the seat 31 into the second position, thus facilitating the alignment between the prosthesis 12 and the channel Z.

In the loading position, the pressure element 16 crosses the chamber C and is close to pushing the prosthesis 12 inside the tubular element 7, i.e. inside the channel Z (see the final time instant of the position in FIG. 6)

The movement of the pressure element 16 from the rest position to the retreated position and from the retreated position to the loading position occurs through the action of the movement means 21 which will be better described below.

In a second embodiment, the pressure element 16 is initially housed inside the applicator pistol 2 while in the cartridge 5, inside the tubular element 7, a closure element 15 is present.

The seat 31 is positioned on top of a passage 35 obtained in the support body 8, in which the locking element 15 is positioned. In particular, the locking element 15 is positioned inside the aforesaid passage 35 during the initial instants, before the applicator pistol 2 starts to function.

Still more particularly, the locking element 15 is situated inside the tubular element 7 and at least partly crosses the interior of the chamber C in order to hinder the action of the pusher means 13.

In such time instant, the seat 31 is constrained in the first position and the pressure element 16 is placed in a trigger position, in which it is disconnected from the channel Z and from the chamber C (FIG. 3).

Also in this embodiment, the movement of the pressure element 16 is entrusted to the first movement means 21.

Said movement means 21 facilitate the movement of the pressure element 16 from the trigger position to an advance position, from the advance position to a retreated position and from the retreated position to a loading position.

The pressure element 16, from the trigger position to the advance position, slides under the action of the first movement means 21 inside the tubular body 7 in order to expel locking element 15.

In such time instant, the pressure element 16 pushes the closure element 15 outside the tubular element 7 and the passage 35 mentioned above is simultaneously and progressively occupied by the pressure element 16.

In this manner, the pusher element 13 continues to be opposed, this time by the pressure element 16 which occupies the position previously occupied by the closure element 15, and the seat 31 remains in its first position.

When the pressure element 16 has reached the advance position (FIG. 4), this will have crossed the entire chamber C, the channel Z of the tubular element 7 until it exits outward from the latter by a pre-established amount D1.

As is visible from the enclosed figures, the rest position of the first embodiment of the device 1 illustrated in FIG. 4 coincides with the advance position of the second embodiment of the device.

The penetration portion of the pressure element 16 inside the channel Z will be sized in a manner such to allow the pointed end 17 to exit from the tubular element 7, in a manner so as to allow both the automatic expulsion of the closure element 15 from the tubular element 7 and the subsequent possibility of penetrating the body tissue through the pointed end 17 of the pressure element 16.

The pressure element 16, having reached the advance position, will hinder the action of the pusher element 13.

Subsequently, according to the modes already described in the first embodiment, the pressure element 16 will proceed under the action of the movement means 21 to be moved from the advance position to the retreated position and from the retreated position to the trigger position.

In the retreated position, no component will be present in the chamber C, neither the locking element 15 (previously expelled) nor the pressure element 16 (situated in the retreated position), i.e. inside the passage 35 arranged underneath the seat 31, the prosthesis 12 can be moved, under the action of the pusher element 13, from the first position to the second position.

Having reached the second position, the prosthesis 12 and in particular the axis H-H of the seat 31 will coincide with the axis X-X of the tubular body 7.

In such position, the pressure element 16, under the action of the first movement means 21, reaches the loading position and proceeds with the insertion of the prosthesis 12 inside the channel Z until the expulsion of the same from the tubular element 7.

Second movement means 25 are also provided for, common to both embodiments, in order to move the tubular element 7 with respect to the pressure element 16. The second movement means 25 can comprise a second motor 26, e.g. of electric type, adapted to rotate a second worm screw 27. A slide 28, which supports the cartridge 5, is engaged with the second motor 26.

The first motor 22 and the second motor 26 are fixed to a support flange 29 arranged in a rear region of the operative portion 4 of the applicator pistol 2.

The first worm screw 23 and the second worm screw 26 are preferably parallel to each other and are extended along a main size of the operative portion 4. The first worm screw 23 and the second worm screw 26 are arranged on both sides of the pressure element 16, when the latter is received inside the applicator pistol 2.

The device 1 also comprises a control unit 30 for controlling the first movement means 21 and the second movement means 25. In the depicted example, the control unit 30 is housed inside the grasping portion 3 of the applicator pistol 2. The control unit 30 allows precisely programming the travel of the first movement means 21 and of the second movement means 25, and consequently of the pressure element 16 and of the tubular element 7.

Activation means, common to both embodiments, can be provided for activating the first movement means 21 and the second movement means 22. The activation means can comprise a button 32 positioned in the grasping portion 3 of the applicator pistol 4. In one version, the activation means can also comprise a rear button 34, shown in FIG. 8, positioned in a rear region of the operative portion 4.

The device 1 can also comprise signaling means 33, common to both embodiments, adapted to signal the status of the device 1 to an operator. The signaling means 33 can for example inform the operator that the device 1 is ready to carry out a certain operation, or that the operator must wait several seconds before carrying out any operation because the device 1 is currently working. The signaling means 33 can be positioned in a rear region of the operative portion 4. The signaling means 33 can be of optical type and can comprise one or more colored LED.

During functioning, the operator must actuate preliminary operations according to the device 1 with which one intends to carry out the operation.

A first device 1, obtained by utilizing the first embodiment, provides for an applicator pistol 2 and a cartridge 5 already assembled together.

The device 1, according to the first embodiment, reaches an initial operative position shown in FIG. 4 in which the pressure element 16 is in the rest position.

In this manner, it is possible to avoid employing the closure body 15, since the channel Z of the tubular body 7, and the chamber C, of the cartridge 5, are isolated from each other by the pressure element 16; the latter results at least partly inserted in the chamber C, and thus the pusher element 13 is prevented from bringing the seat 31 of the prosthesis 12 from the first position to the second position.

The pressure element 16 is in the rest position, in which it exits from the tubular element 7 with its pointed end 17.

In such position, the pressure element 16, also situated inside the chamber C of the support body 8, hinders the pusher element 13, maintaining the seat 31 in the first position.

In the rest position, the seat 31, situated in the first position, is pushed by the elastic means 14 against the pressure element 16 which blocks the movement S of the seat 31 from the first position to the second position. In such time instant, there is no liquid communication between the channel Z and the chamber C, i.e. the prosthesis 12 is isolated.

In this step, the device 1, in particular the tubular element 7 is ready to be inserted in the body tissue.

The symmetric conformation of the pointed end 17 will facilitate the opening of the body tissue and thus the insertion of the tubular element 7.

The insertion of the tubular element 7 is further facilitated by the surface treatment of the external portion which is coated with TEFLON® or ceramic material. Such coating type reduces the friction between the tubular element 7 exterior and the tissue, in a manner so as to prevent the tubular element 7 exterior from adhering the tissue.

Once the correct position for the release of the prosthesis is reached, the operator activates the activation means, for example by pressing the button 32.

The control unit 30 automatically recognizes, through the use of known electronic signaling devices, that the device 1 utilizes the first embodiment, i.e. it is of the type with cartridge and applicator pistol already assembled by the manufacturer.

The control unit 30 drives the first motor 22 which correspondingly rotates the first worm screw 23 in a direction such that the carriage 24 moves back inside the operative portion 4. The pressure element 16 is consequently moved in a retreated direction F1.

The first movement means 21 are programmed for moving the pressure element 16 back.

In this manner, the pressure element 16 first exits from the interior of the tubular element 7 and subsequently moves back until it exits from the chamber C.

Such operative position is defined upon the attainment of the retreated position.

In such position, the seat 31 and in particular the prosthesis 12 are moved along the movement direction S, being moved from the first position to the second position.

Said movement occurs under the action of the pusher element 13 which encounters no more obstacles.

Figure 5:
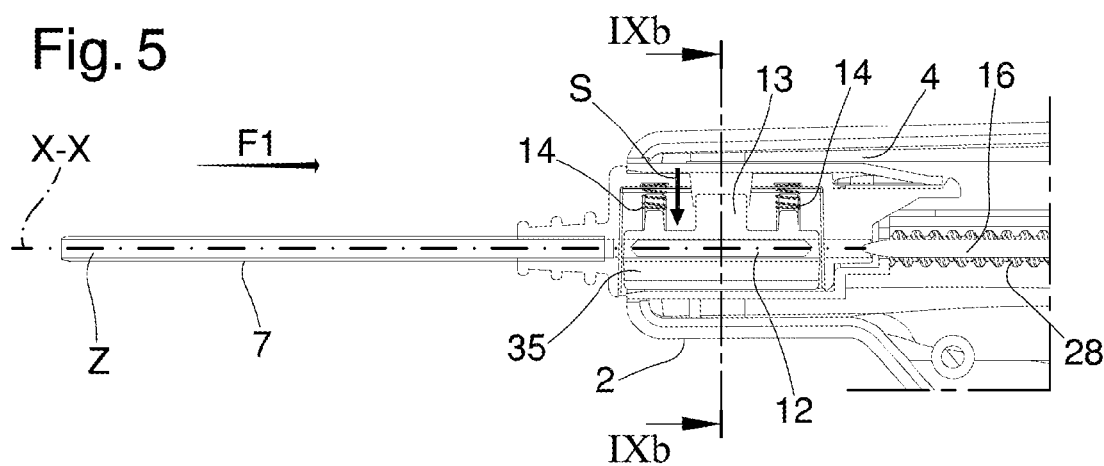
FIG. 5 is a section like that of FIG. 3, showing the front portion of the device of FIG. 1 in a back position.

In such time instant, the prosthesis 12 is situated with its axis Y-Y aligned with the axis X-X of the chamber Z. Such position is shown in FIG. 5.

After the pressure element 16 has reached the retreated position, the control unit 30 once again activates the first movement means 21 for advancing the pressure element 16 in an advancement direction F, in order to reach the loading position.

The subsequent driving of the movement means 21 and 22, after the pressure element 16 has reached the loading position, will be described in the second embodiment of the device 1.

A second device 1, obtained by employing the second embodiment, provides for an applicator pistol 2 and a cartridge 5 initially disassembled and packaged inside separate casings, so as to both be in sterile conditions.

The pressure element 16 is positioned inside the applicator pistol 2 completely disconnected from the channel Z and from the chamber C.

Said pressure element 16 is therefore positioned in the trigger position.

The cartridge 5 contains at its interior the locking element 15, at least partly crossing the chamber C, in order to hinder the pusher element 13, maintaining the seat in the first position.

The cartridge 5 is mounted on the applicator pistol 2, positioning the support body 8 inside the hole 9 and pushing the cartridge 5 towards the interior of the operative portion 4. In this manner, the fixing means 10 associated with the cartridge 5 are engaged with the corresponding fixing means obtained in the applicator pistol 2, e.g. with the laminar element 11, and the cartridge 5 results locked on the applicator pistol 2.

The initial operative position shown in FIG. 3 is thus reached. In this position, the pressure element 16 is still housed inside the applicator pistol 2 in the trigger position, at the rear of the cartridge 5. The locking element 15 is positioned inside the support body 8, inside the chamber C, and also partly inside the tubular element 7, inside the channel Z. The locking element 15 closes the passage Z arranged below the seat 31, thus providing the liquid communication between the channel Z and the seat 31 and overcoming the resistance of the elastic means 14. In other words, the locking element 15 hinders the movement S of the pusher element 13 which remains in the first position.

In such time instant, the seat 31 is isolated by the channel Z of the tubular element 7.

The operator now activates the activation means, for example by pressing the rear button 34 and maintaining it pressed until the first signaling element is turned on, e.g. a red LED, of the signaling means 33. The control unit 30 is thus informed that the cartridge 5 was correctly positioned in the applicator pistol 2.

The control unit 30 activates first movement means 21 for advancing the pressure element 16 inside the tubular element 7. In particular, the control unit 30 acts on the first motor 22, which in turn drives the worm screw 23 in rotation. The latter moves the carriage 24 towards the front terminal region 6 of the applicator pistol 2. The pressure element 16, which is fixed with respect to the carriage 24, is thus advanced along an advancement direction F and penetrates inside the tubular element 7 in order to be moved from the trigger position to the advance position.

Here, the pressure element 16 interacts with the locking element 15.

The pressure element 16 pushes the locking element 15 and its pointed end 17 is inserted inside the hollow terminal section 15a, facilitating the engagement of the pressure element 16 with the locking element 15.

The coupling between the pointed end 17 and terminal section 15a facilitates the movement of the locking element without pointing inside the tubular element.

During the movement of the pressure element 16 from the trigger position to the advance position, the pressure element 16 continues to progressively advance inside the tubular element 7, the pressure element 16 pushes the locking element 15 along the advancement direction F until it completely exits through the open end 18.

The first movement means 21 are programmed for moving the pressure element 16 along a controlled travel. Indeed, the first movement means 21 are programmed for being stopped when the pointed end 17 of the pressure element 16 projects outside the tubular element 7 by a pre-established amount D1. In such a manner, the advance position shown in FIG. 4 is completed; in such position, the device 1 is ready to interact with the body of the patient.

The operator can then penetrate the body tissue in which the prosthesis 12 must be inserted, at the desired position. It is thus possible to introduce, in the body tissue, first the portion of the pressure element 16 that exits from the tubular element 7, and then, by continuing to press the pistol 2 towards the patient, a portion of the tubular element 7 having a desired length.

It is observed that, since the pointed end 17 of the pressure element 16 in this step exits from the tubular element 7, the body tissue is penetrated by the pressure element 16, which behaves like a needle.

In addition, the axial-symmetric conformation of the pointed end 17 facilitates an improved opening of the tissues.

The coating made of Teflon® or ceramic material of the external surface of the tubular element 7 reduces the friction as much as possible and contributes to the ease of insertion of the tubular element itself in the body tissue.

In the advance position shown in FIG. 4, the prosthesis 12 is still housed inside the seat 31 which does not result in liquid communication with the channel Z. Indeed, the pressure element 16, which is positioned inside the tubular element 7 in the advance position, has substituted the locking element 15 in contact with the prosthesis 12. The pressure element 16 therefore maintains the prosthesis 12 pushed upward, overcoming the force exerted downward by the elastic means 14.

When the pressure element 16 has pierced body tissue and the tubular element 7 has reached the position in which the prosthesis 12 must be implanted, the operator can act on the activation means for once again activating the first movement means 21. For such purpose, the operator can, for example, press the button 32 provided on the grasping portion 3 of the applicator pistol 2.

The control unit 30 drives the first motor 22 in a rotation direction opposite that in which the first motor 22 was driven for expelling the locking element 15. The first motor 22 correspondingly rotates the first worm screw 23 in a direction such that the carriage 24 moves back inside the operative portion 4. The pressure element 16 is consequently moved in a retreated direction F1 opposite the advancement direction F, while the operator maintains the applicator pistol 2 in contact with the patient body, such that the tubular element 7 remains inside the body tissue. In this manner, the pressure element 16 first returns inside the tubular element 7 and then moves back inside the operative portion 4, until it reaches the retreated position in which the passage Z arranged below the seat 31 is left free. Such position is shown in FIG. 5.

When the pressure element 16 is situated in the retreated position, the prosthesis 12 is moved from the seat 31 inside the passage aligned with the tubular element 7, due to the force exerted by the pusher element 14. Such force is no longer opposed by the pressure element 16. The prosthesis 12 is now aligned with the pressure element 16. In particular, the axis H-H of the seat 31 is aligned with the axis X-X of the channel Z.

After the pressure element 16 has reached the retreated position, the control unit 30 once again activates the first movement means 21 for advancing the pressure element 16 in the advancement direction F in order to reach the loading position. The pointed end 17 of the pressure element thus comes into contact with the rear end 20 of the prosthesis 12 and, as the pressure element 16 is progressively moved along the advancement direction F, the prosthesis 12 is pushed towards the open end 18 of the tubular element 7. The first movement means 21 are programmed for advancing the pressure element 16 until the front end 19 of the prosthesis 12 is situated at a pre-established distance D from the open end 18 of the tubular element 7, the prosthesis 12 still being housed inside the tubular element 7. The distance D can be substantially zero, as shown in the example of FIG. 6, in which case the front end 19 of the prosthesis 12 is substantially flush with the open end 18 of the tubular element 7.

In an alternative, non-depicted version, the distance D could be greater than zero, in which case the pressure element 16 would be stopped when the front end 19 of the prosthesis 12 is still inside the tubular element 7.

After the pressure element 16 has positioned the prosthesis 12 at the desired distance D from the open end 18, reaching the advance position shown in FIG. 6, the control unit 30 activates the second movement means 25. In particular, the control unit 30 acts on the second motor 26, which rotates the second worm screw 27 so as to move the slide 28 back in the retreated direction F1. Since the slide 28 is fixed with respect to the cartridge 5, the entire cartridge 5 is moved back inside the operative portion 4. Consequently, the tubular element 7 is moved in the back direction F1 with respect to the pressure element 16, which instead remains in a fixed position.

Figure 7:
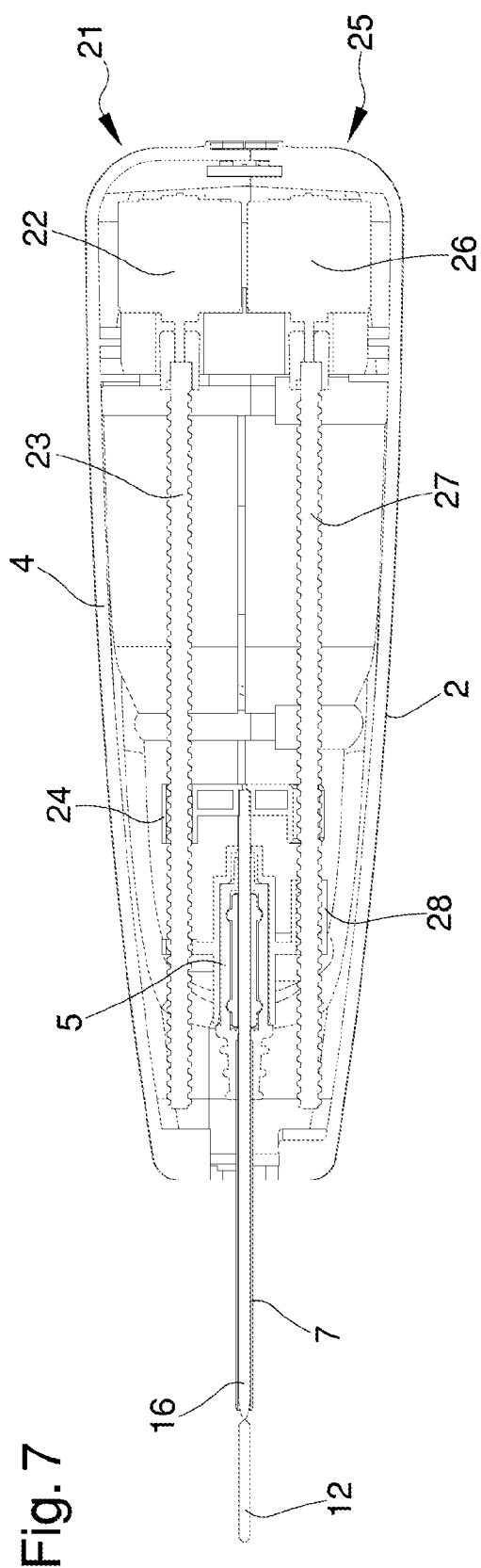
FIG. 7 is a section like that of FIG. 4, showing the device of FIG. 1 in a release position.

The release position shown in FIG. 7 is thus achieved; in this position, the prosthesis 12 is released in the body tissue in which the pressure element 16 is inserted.

The second movement means 25 are programmed for stopping the travel of the pressure element 16 in the retreated direction F1 when the rear end 20 of the prosthesis 12 has exited from the open end 18.

In particular, the second movement means 25 can be programmed for moving the tubular element 7 back an amount equal to the longitudinal size DL of the prosthesis 12, increased by the distance D shown in FIG. 6. In this manner, the tubular element 7 is stopped when its open end 18 is flush with the rear end 20 of the prosthesis 12.

After the prosthesis 12 was released in the body tissue, it is possible, particularly if the tubular element 7 does not contain other prostheses, to once again advance the tubular element 7 in order to bring the cartridge 5 into the initial position, due to the second movement means 25. The first movement means 21 can instead once again move the pressure element 16 back inside the operative portion 4, such that the pressure element 16 is disengaged from the cartridge 5. In this manner, the final position shown in FIG. 8 is reached. The operator can now remove the cartridge 5 from the applicator pistol 2.

The first movement means 21 and the second movement means 25 allow precisely controlling the sequence with which the pressure element 16 and the tubular element 7 are moved as well as the respective travels/paths.

In this manner, it is possible to prevent, in the release position shown in FIG. 7, the tubular element 7 from moving back too little or too much with respect to the pressure element 16, causing a partial release of the prosthesis 12.

Even if the cartridge 5 shown in FIGS. 1-8 contains a single prosthesis 12, it is possible, in a non-depicted version, to provide for cartridges containing multiple prostheses, e.g. positioned on top of each other in a manner such to be introduced in successive instants inside the tubular element 16. Such prostheses can then be implanted in the body of the patient by repeating the previously described cycle several times.

The invention claimed is:

1. A device for implanting a prosthesis in a body tissue, comprising:
   a tubular element, at its own interior defining a channel (Z) having extension direction along an axis (X-X) and cross section of area (A), within which a prosthesis can slide that has a cross section of area (T);
   a pressure element movable inside the channel (Z) for moving said prosthesis;
   characterized in that it comprises:
   a cartridge provided with a chamber (C), in communication with the channel (Z), comprising a seat, preferably with extension direction along an axis (H-H) and cross section of area (V), housing the prosthesis and movable inside the chamber (C);
   a pusher element operating on the seat in order to facilitate the movement of the seat inside the chamber (C) from a first position, in which the area (V) of the cross section of the seat is outside the area (A) of the cross section of the tubular element, the seat not facing the channel (Z), to a second position, in which the area (V) of the cross section of the seat at least partly intersects the area (A) of the cross section of the tubular element, inducing a communication between the channel (Z) and the seat suitable for facilitating the insertion of the prosthesis inside the channel (Z) upon command of the pressure element.

2. The device according to claim 1, characterized in that said prosthesis, housed inside the seat, is movable under the action of the pusher element from the first position, in which the area (T) of the cross section of the prosthesis is outside the area (A) of the cross section of the tubular element, to the second position, in which the area (T) of the cross section of the prosthesis is entirely contained inside the area (A) of the cross section of the tubular element in order to facilitate the insertion of the prosthesis inside the channel (Z) through the pressure element.

3. The device according to claim 2, characterized in that said prosthesis preferably has an extension direction along an axis (Y-Y).

4. The device according to claim 3, characterized in that said prosthesis is movable, under the action of the pusher element, from the first position, in which the axis (Y-Y) is misaligned with the axis (X-X) of the channel (Z), to the second position, in which the axis (Y-Y) is aligned with the axis (X-X) of the channel (Z).

5. The device according to claim 1, characterized in that said pressure element is situated, in a first embodiment, in a rest position in which it is inserted inside the chamber (C), in order to hinder the pusher means, maintaining seat in the first position, so that it exits outward from the channel (Z) for a pre-established amount (D1).

6. The device according to claim 5, characterized in that said pressure element, when situated in the rest position, is movable under the action of first movement means from a retreated position, in which the pressure element is disconnected from the chamber (C) in order to allow the seat to reach the second position, to a loading position, in which the pressure element crosses the chamber (C), pushing the prosthesis inside the tubular element.

7. The device according to claim 6, characterized in that said first movement means are programmed for moving the pressure element back outside the chamber (C) in order to generate a communication between the seat and the channel (Z) and to allow the pusher element to push the seat into the second position, facilitating the alignment between the prosthesis and the channel (Z).

8. The device according to claim 6, characterized in that said pusher element is defined by elastic means suitable for generating a thrust of the seat from the first position to the second position, said pressure element, when situated in the retreated position, frees the elastic means, allowing the seat to reach the second position.

9. The device according to claim 5, characterized in that said pusher element is defined by elastic means suitable for generating a thrust of the seat from the first position to the second position, said pressure element, when situated in rest position, opposes the thrust exerted by the elastic means on the seat, constraining the latter in the first position.

10. The device according to claim 1, characterized in that it comprises, in a second embodiment, a closure element situated inside the tubular element, at least partly crossing the interior of the chamber (C) in order to hinder the action of the pusher means, thus maintaining the seat in the first position; said pressure element being positioned in a trigger position in which it is disconnected from the channel (Z) and from the chamber (C).

11. The device according to claim 10, characterized in that said pressure element, when situated in the trigger position, is movable under the action of first movement means from an advance position, in which the pressure element crosses the chamber (C) and the channel (Z) of the tubular element, causing the outward exit of the closure element from the tubular element, to a retreated position, in which the pressure element is disconnected from the chamber (C) in order to allow the seat to reach the second position, to a loading position, in which the pressure element crosses the chamber (C), pushing the prosthesis inside the tubular element.

12. The device according to claim 11, characterized in that said first movement means are programmed for advancing the pressure element inside the tubular element in order to cause the outward exit of the closure element from the latter and the consequent removal of the same.

13. The device according to claim 11, characterized in that said pusher element is defined by elastic means suitable for generating a thrust of the seat from the first position to the second position, said pressure element, when situated in the advance position, opposes the thrust exerted by the elastic means on the seat, constraining the latter in the first position.

14. The device according to claim 10, characterized in that said pusher element is defined by elastic means suitable for generating a thrust of the seat from the first position to the second position, said closure element, when inserted in the tubular element, opposes the thrust exerted by the elastic means on the seat, constraining the latter in the first position.

15. The device according to claim 1, characterized in that said pusher element is defined by elastic means suitable for generating a thrust of the seat from the first position to the second position.

16. The device according to claim 15, characterized in that said elastic means cause a thrust of the seat along a direction (S) incident on the axis (X-X) of the channel (Z).

* * * * *